United States Patent [19]

Photis et al.

[11] 4,234,739

[45] Nov. 18, 1980

[54] METHOD FOR PREPARING GLYOXYLIC ACIDS AND DERIVATIVES THEREOF

[75] Inventors: James M. Photis, Ridgefield, Conn.; Fred S. Eiseman, Basking Ridge; Sidney M. Gister, Highland Park, both of N.J.

[73] Assignee: Stauffer Chemical Company, Westport, Conn.

[21] Appl. No.: 966,673

[22] Filed: Dec. 5, 1978

[51] Int. Cl.$^3$ .................... C07C 69/66; C07C 59/153
[52] U.S. Cl. ..................................... 560/51; 560/126; 560/174; 562/459; 562/508; 562/577; 564/169
[58] Field of Search ....................... 560/51, 126, 174; 562/459, 508, 577; 260/558 R

[56] References Cited

U.S. PATENT DOCUMENTS 4,069,252  1/1978  Finderson et al. .................... 560/51

FOREIGN PATENT DOCUMENTS 2708189  8/1978  Fed. Rep. of Germany ............ 560/51

*Primary Examiner*—Paul J. Killos
*Attorney, Agent, or Firm*—William C. Gerstenzang

[57] ABSTRACT

Glyoxylic acids or derivatives thereof are prepared by reacting an acyl nitrile compound with concentrated sulfuric acid in the presence of halide anion to form a first reaction product and then further reacting the first reaction product with a compound of the general formula ROH to form the desired glyoxylic acid or glyoxylic acid derivative.

16 Claims, No Drawings

METHOD FOR PREPARING GLYOXYLIC ACIDS AND DERIVATIVES THEREOF

BACKGROUND OF THE INVENTION

The present invention relates to a method for preparing glyoxylic acids and their derivatives. More particularly, the present invention relates to a method of preparing these compounds from acyl nitrile compounds.

Glyoxylic acids and their derivatives serve many specialized applications in the chemical arts. Amongst the most important of these is their use as photoinitiators and as intermediates for preparing photoinitiators.

U.S. Pat. No. 4,038,164 discloses the use of certain glyoxylic acid derivatives as photoinitiators. The particular compounds referred to by the patent are arylglyoxylate, ring-substituted arylglyoxylate and heterocyclic glyoxylate compounds. It is suggested that these compounds be prepared by the methods of U.S. Pat. Nos. 3,5312,737 and 3,065,259.

The several preparation routes disclosed in the first of these patents, U.S. Pat. No. 3,532,737; all utilize glyoxylic acid as a starting material. This compound is difficult to prepare and is not readily available.

The second patent, U.S. Pat. No. 3,065,259, requires the use of an organo-metallic compound and lithium halide; the reaction involved is highly exothermic and yields are relatively low.

It is also suggested that one of the preferred compounds of U.S. Pat. No. 4,038,164; namely the methyl ester of phenylglyoxylic acid, be prepared by the reaction of methyl oxalyl chloride with benzene in the presence of aluminum trichloride. While this method produces results which are generally acceptable, the relatively high cost of the required alkyl oxalyl chloride and the relatively low yield of the process are objectionable factors.

Another process which has been suggested is the oxidation of mandelic acid to form phenyl glyoxylic acid which is then esterified with methyl alcohol. This process is objectionable because the yields are low and the process produces excessive quantities of by-products which cannot be recycled.

U.S. Pat. No. 4,069,252 discloses yet another route for making these compounds. Example 4 of the patent teaches that phenylglyoxylic acid ethyl ester can be prepared by refluxing a solution of benzoyl cyanide in ethanol, in the presence of HCl, for 5 hours and then distilling-off excess ethanol. This method, however, is less than satisfactory because it leads predominantly to ethyl benzoate.

It is apparent from the foregoing that a need exists for a method for preparing glyoxylic acids and derivatives thereof which utilizes readily available raw materials and produces the desired products in high yields. We have found a new method for the preparation of glyoxylic acids and their derivatives which eliminates most of the aforementioned objections.

SUMMARY OF THE INVENTION

It is an object of the present invention to provide an improved method for the preparation of glyoxylic acids and their derivatives which is fast, efficient and does not require the use of starting materials which are difficult to obtain.

It is yet another object of the present invention to provide a method for the hydrolysis of acyl nitrile compounds wherein cleavage of the cyano group from the compound being hydrolyzed is avoided.

It has now been found that acyl nitrile compounds can be hydrolyzed without cleavage of cyano groups from the compounds, by reacting the nitrile compound with concentrated sulfuric acid in the presence of halogen anion. The product of this reaction can then be further reacted to form a glyoxylic acid or a glyoxylic acid derivative. As an example, the reaction product can be further reacted with an alcohol to form the ester, or water to form the acid.

DETAILED DESCRIPTION OF THE INVENTION

In accordance with the present invention, there is provided a method for preparing glyoxylic acids and their derivatives which comprises the steps of (a) reacting the acyl nitrile compound with concentrated sulfuric acid in the presence of halogen anion to form a first reaction product; and (b) further heating the first reaction product to form the desired glyoxylic acid or glyoxylic acid derivative.

One novel feature of the present invention resides in the first step (step a) of the method. More specifically it resides in the concept of reacting an acyl nitrile compound with concentrated sulfuric acid in the presence of halide ion without cleaving the cyano function from the compound to form a reaction product which can then be subjected to partial or complete hydrolysis and/or alcoholysis. Thus, for example, where the desired final product is an ester, the first reaction product can be further reacted with the appropriate alcohol to form the ester; where the desired final product is an amide, the first reaction product can be poured over ice and the amide product precipitated out; where the desired final product is an acid, the first reaction product can be reacted with water to form the acid.

Thus, in one embodiment, the invention comprises a method for producing an ester of an acyl nitrile compound without cleaving the cyano function which comprises the steps of (a) reacting the acyl nitrile compound with concentrated sulfuric acid in the presence of halogen anion to form a first reaction product; and (b) forming a mixture of the first reaction product with a compound of the general formula ROH, wherein R is hydrogen, a straight or branchedchain hydrocarbon, or aralkyl; provided, however, that ROH is not a tertiary alcohol; and heating the mixture at a temperature and for a time sufficient to form the ester.

The present invention is particularly useful for preparing arylglyoxylate products, which are known to be effective photoinitiators in the polymerization of olefins. In a particularly preferred embodiment, therefore, the invention comprises a method for preparing an arylglyoxylate from an aroyl nitrile compound which comprises the steps of (a) reacting the aroyl nitrile compound with concentrated sulfuric acid in the presence of halogen anion to form a first product; and (b) reacting the first reaction product with an alcohol to form the arylglyoxylate; provided, however, that the alcohol is not a tertiary alcohol.

The alcohol can be virtually any alcohol which is capable of reacting with the first reaction product. Tertiary alcohols, however, are excluded because they generally decompose under the conditions necessary for esterification.

Particularly preferred alcohols are methanol and ethanol.

The acyl nitrile compounds which are used to prepare glyoxylate acids and derivatives thereof in accordance with the method of the present invention are those represented by the general formula:

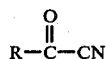

wherein R represents optionally substituted alkyl with from 1 to about 8 carbon atoms, optionally substituted cycloalkyl with 3 to about 12 carbon atoms, or optionally substituted aryl, or an optionally substituted 5-membered or 6-membered heterocyclic radical, which additionally can be fused to a benzene ring. As used herein, the term aryl means one or more benzene rings either with or without substituents such as alkyl, alkoxy, halogen and the like.

The preferred acyl nitrile compounds which are used to prepare glyoxylic acids and derivatives thereof in accordance with the method of the present invention are those wherein R is an optionally substituted aryl group. In these compounds, the double-bonded oxygen and the aryl radical cause the adjacent cyano group to become highly polarized and very susceptible to cleavage from the compound. Because of this, the cyano function is often cleaved from the compound by the prior art methods.

For example, when pure benzoyl cyanide (i.e., containing essentially no halide ion or halide ion source, such as benzoyl chloride) is reacted with concentrated sulfuric acid and then esterified by further reaction with methanol, the cyano group is cleaved and methyl benzoate is formed as follows:

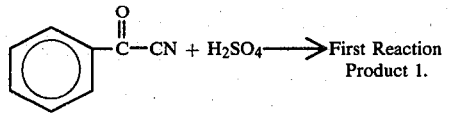 I

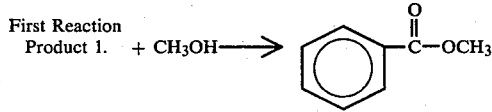 II

When the nitrile compound is reacted in accordance with the method of the present invention, however, cleavage of the cyano group is avoided. More specifically, when benzoyl cyanide is reacted with concentrated sulfuric acid in the presence of halogen anion a first reaction product is formed which, when esterified by reaction with methanol, forms methyl phenylglyoxylate instead of methyl benzoate as follows:

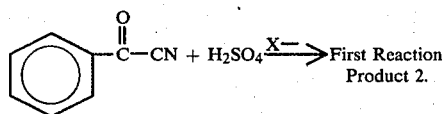 III

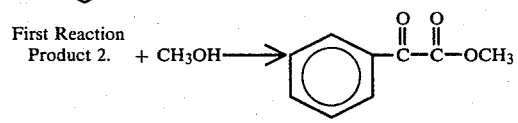 IV

The present invention, therefore, provides a simple, direct and effective method for preparing methyl phenylglyoxylate, a compound known in the art as an important photoinitiator for use in the polymerization of olefins. It is apparent that other alcohols, such as ethanol, propanol and the like can be substituted for the methanol in the illustrated reaction scheme to produce the corresponding esters.

The present invention also provides a simple, direct and effective method for preparing glyoxylic acids. Thus, in the reaction scheme illustrated above, water can be substituted for the alcohol and the final product will then be the acid rather than the ester, as follows:

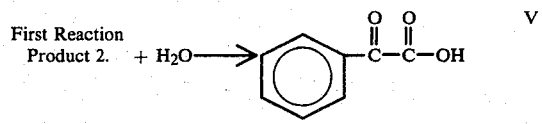 V

The process of the present invention can also be used to prepare amide derivatives of glyoxylic acids (i.e., glyoxyamides). These glyoxyamides can be prepared by reacting an acyl nitrile compound with concentrated sulfuric acid, as shown in Reaction III above, and then pouring the product over ice before it can undergo further reaction with water (present in the sulfuric acid) to form a glyoxylic acid in accordance with Reaction V. As will be understood by those skilled in the art, the amount of time required to enable Reaction III to reach substantial completion without permitting reaction V to proceed to a substantial extent will vary in accordance with several factors, such as the particular acyl nitrile being reacted, the halogen anion concentration, reaction temperature and the like. The determination of the time required under any particular set of conditions is well within the skill of the art.

The amount of concentrated (i.e., from about 70 wt. % to about 90 wt. % $H_2SO_4$) sulfuric acid used in the practice of the present invention ranges from about 0.5 to about 1.5 molar equivalents based on the molar quantity of nitrile compound being reacted. The use of greater amounts is not harmful to the process.

The halide anion which is present in the reaction mixture during the reaction is selected from the group consisting of fluoride, chloride, bromide and iodide. Chloride and bromide anion are preferred because of their effectiveness in promoting the desired reaction.

The halide anion may be introduced into the reaction mixture as a gas, such as HBr, HCl and the like; a salt such as NaBr, NaCl; or any other convenient form.

The halide ion is included in the reaction mixture in catalytic quantities. The specific amount used can therefore vary in accordance with many factors such as the specific acyl nitrile compound being reacted, the particular halide anion being used, the reaction temperature and the desired rate of reaction.

When using halide anion in the form of a gas, such as HCl or HBr, it can be difficult to ascertain the quantity of anion present in the reaction mixture at any particular time. The anion is generally added to the reaction mixture by bubbling gas through the reaction mass. When the gas is bubbled through the reaction mass, not all of the gas is absorbed by the reaction mixture—some escapes. The rate of reaction is best controlled by controlling the rate at which the gas is fed to the reaction mixture.

In general satisfactory results will be achieved with a halide anion concentration ranging from about 0.05 equivalents to about 1.5 equivalents, based on molar equivalents of nitrile compound in the reaction mixture.

Greater concentrations are not harmful to the process however.

The temperature at which the reaction can be conducted ranges from about −10° to about 80° C., although a temperature ranging from about 20° C. to about 70° C. is preferable. Temperatures above about 80° C. should be avoided because an exothermic decomposition reaction can occur at temperatures above 80° C. The decomposition reaction adversely affects the progress of the reaction and the yields of the desired product. At temperatures below about −10° C., the reaction rate is slow.

Although not a necessary ingredient, it is preferable to include an acylating agent in the reaction mixture. The presence of such an agent controls the reaction so that the exotherm is not as sharp as it would otherwise be and also minimizes the formation of alternative products (i.e., where methyl phenylglyoxylate is being prepared, the "alternative product" which is minimized by the presence of the acylating agent is methyl benzoate).

Acylating agents which can be used include, but are not limited to, acetic anhydride, benzoyl chloride, benzoic anhydride, propionic anhydride and and like; although acetic anhydride is preferred.

The amount of acylating agent used ranges from about 0.5 to about 1.5 molar equivalents based on the amount of acyl nitrile compound being reacted. Greater amounts, however, are not harmful to the process. The most satisfactory results, however, in terms of exotherm suppression and minimal formation of alternative products, are achieved using at least a full molar equivalent of the acylating agent. Therefore it is preferred to use about 1 molar equivalent of the acylating agent.

In the practice of the present invention, the acyl nitrile compound is first reacted with concentrated sulfuric acid in the presence of a halide anion and, optionally, in the presence of an acylating agent, to form a first reaction product. The first reaction product is then further treated to produce the desired glyoxylic acid or glyoxylic acid derivative. The treatment of the first reaction product is a conventional step and is easily within the skill of the art, once given the starting material prepared in accordance with the novel aspect of the present invention. Such further treatment includes, without limitation, the further reaction of the first reaction product with an alcohol to form an ester; pouring the first reaction product over ice to precipitate an amide compound, or further reaction of the first reaction product with water to form an acid.

Although not necessary to the practice of the invention, it is preferable to conduct the reaction between the acyl nitrile compound and sulfuric acid in the presence of a hydrocarbon solvent, such as hexane. The hydrocarbon solvent provides a means for reflux-cooling the reaction mixture, thereby providing an additional mechanism for controlling reaction temperature, and preventing an exothermic decomposition from taking place. Thus, with the hydrocarbon solvent present in the reaction mixture, should the reaction temperature reach the boiling point of the hydrocarbon solvent, reflux of the solvent can be initiated to help control the temperature.

In order that the present invention be more fully understood, the following examples are given by way of illustration. No specific details or enumerations contained therein should be construed as limitations to the present invention except insofar as they appear in the appended claims. All parts and percentages are by weight unless otherwise specifically designated.

EXAMPLE 1

In a set of experiments 7.0 grams of orthomethylbenzoyl cyanide was added to 7.0 grams of 85% sulfuric acid containing about 0.5 grams of sodium halide and the mixture was stirred and heated between 60° C. and 70° C. for 5 minutes. Methyl alcohol was then added in excess and the homogeneous mixture was refluxed at atmospheric pressure for 5 minutes.

The product was isolated by addition of water, and analyzed by infrared spectroscopy.

The sodium halides used in the set of experiments were sodium fluoride, sodium chloride, sodium bromide and sodium iodide.

The reaction mixture containing sodium fluoride etched the glass flask in which the reaction was being conducted.

The reaction mixture containing the sodium bromide gave off red fumes.

The reaction mixture containing the sodium iodide became deep purple.

The % yield of methyl o-methyl phenylglyoxylate for each halide is shown below.

| Sodium Halide | % Yield of Methyl o-methyl Phenylglyoxylate |
|---|---|
| None | 0 |
| Na F | 25 |
| Na Cl | 50 |
| Na Br* | 80 |
| Na I | 10 |

*product also contained significant quantities of ketoamide.

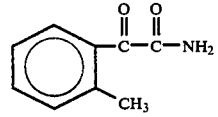

This example shows that halide anions effectively promote the disclosed conversions of aroyl nitrile compounds without cleaving the cyano function, and that chloride and bromide are most effective.

EXAMPLE 2

Benzoyl cyanide in the amount of 6.5 grams was slowly added with stirring to 9.3 grams of 85% sulfuric acid at 30° C. There was no noticeable increase in temperature. It was observed that the two liquids were immiscible. Heating to 35° C. was necessary to prevent solidification of the benzoyl cyanide. Acetic anhydride in the amount of 5.1 grams was slowly added with continued stirring. The addition of the acetic anhydride caused a noticeable increase in temperature. It was observed that the presence of the acetic anhydride brought about complete miscibility of the reaction components at 35° C. Upon cooling a solid formed once again which was identified by infrared spectroscopy as benzoyl cyanide.

The reaction mixture was heated to 35° C. and 50 milligrams of sodium bromide crystals was added. The temperature rose to about 45° C. as a result of this addition of the sodium bromide crystals, and external cooling was applied to maintain the temperature of the reaction mass at about 30° C. After the sodium bromide addition was complete, the reaction mixture was maintained at a temperature ranging from ambient to about 30° C. for 30 minutes, with stirring. At the end of this period, the reaction mixture was poured over ice.

A yellow solid precipitate formed, which was removed by suction filtration and dried to produce a yield of 7.4 grams. This material was found to have a melting point of 89° C. and identified by infrared spectroscopy to be phenylglyoxamide (benzoyl formamide).

This demonstrates that the improved method of the present invention can be used to prepare amide derivatives of glyoxylic acids. This is an important embodiment of the present invention since benzoyl formamide is an effective photoinitiator also.

EXAMPLE 3

Benzoyl formamide, in the amount of 50 grams, was mixed with 10 grams of 85% sulfuric acid and the mixture was heated on a steam bath until all the benzoyl formamide went into solution. The resulting pale yellow solution was cooled and 10 milliliters of absolute methyl alcohol was slowly added. The mixture was heated to reflux temperature and maintained at reflux for about 15 minutes. Water was then added to the mixture and the mixture permitted to settle to two phases.

The lower phase was separated and dried over sodium sulfate to yield 4.6 grams (84% of Theory) of a material which was identified by infrared spectroscopy to be methyl phenylglyoxylate.

This demonstrates that the amide derivatives of glyoxylic acids prepared in accordance with the method of this invention may be easily converted to the ester.

EXAMPLE 4

A five-hundred milliliter three neck round bottomed flask was charged with 65 grams of 98% sulfuric acid. Benzoyl cyanide, in the amount of 65.5 grams, was added over a period of about one minute while maintaining the flask contents at 15° C. with external cooling. Hydrogen chloride gas was then introduced below the surface of the liquid flask contents at a rate of 25-30 milliliters per minute with continuous stirring. Acetic anhydride, in the amount of 51 grams was then added slowly, causing the temperature of the flask contents to rise to 55° C. The hydrogen chloride gas flow was continued for an additional 40 minutes while maintaining temperature at 55° C. and continuing stirring.

The reaction mixture was then added to a solution comprising 65 grams of 98% sulfuric acid in 220 milliliters of absolute methyl alcohol. The resulting mixture was heated to reflux and maintained at reflux temperature for a period of 1.5 hours after which 1 liter of water was added. The resulting two-phase mixture was permitted to settle, after which the lower phase was separated, washed with an aqueous sodium bicarbonate solution and distilled.

Final product yield was 63.1 grams (77% theoretical) of methyl phenylglyoxylate (boiling point 66°-68° C. at 0.15 mm Hg.).

This demonstrates that the method of the present invention can be employed to prepare the esters of glyoxylic acids directly from an acyl nitrile compound in a relatively short period of time.

EXAMPLE 5

Sodium bromide crystals in the amount of 6.5 grams were added to 120 grams of 85% sulfuric acid. This mixture was stirred for about 15 minutes and then the temperature was lowered from ambient to about 10° C. While continuing to stir and to apply external cooling, a solution comprising 85 grams of benzoyl cyanide in 65 grams of acetic anhydride was added over a period of 8 to 10 minutes. Upon completion of this addition the temperature of the reaction mixture was 25° C. External cooling was discontinued and the reaction mixture was stirred for an additional period of 15-20 minutes. At the end of this period the temperature of the reaction mixture had risen to 38° C. The reaction mixture was poured over 500 grams of crushed ice. A yellow precipitate was formed. The yellow precipitate was recovered by suction filtration. Extraction of the filtrate with chloroform produced 21.0 grams of a yellow oil. This yellow oil was found to have an infrared spectrum identical to that of authentic benzoylformic acid (phenylglyoxylic acid).

This demonstrates that the method of the present invention can be practiced to prepare glyoxylic acids.

EXAMPLE 6

A two liter, three-neck, round bottomed flask was charged with 28 milliliters of water and 156 grams of concentrated sulfuric acid. The flask contents were cooled to about 20° C. and 10.0 grams (0.097 moles) of sodium bromide crystals were added. The contents were stirred for about 15 minutes and the temperature was lowered to about 10° C.

An addition funnel was charged with 102 grams (1.0 grams) of acetic anhydride and then a solution of 130 grams (0.99 mole) of undistilled benzoyl cyanide in 300 milliliters of hexane was decanted from a small quantity of insoluble tar into the addition funnel. The contents of the addition funnel formed a two-phase mixture.

The contents of the addition funnel were then added to the flask with stirring and external cooling, over a period of 22 minutes. The temperature of the flask contents increased to 35° C. External cooling was continued until the temperature was reduced to 24° C. Stirring was then continued under ambient conditions for an additional period of about 2.5 hrs. During this time the temperature increased to 31° C.

Absolute methyl alcohol in the amount of 200 milliliters was then added to the flask contents over a period of 5 minutes. The temperature increased to the boiling point of the reaction mixture (53° to 54° C.). External heating was applied and 150 milliliters of volatiles was distilled from the reaction mixture. Heating and stirring were continued under reflux for a period of 2.75 hours. Water, in the amount of 600 milliliters, was then added to the flask resulting in the formation of a two-phase mixture. The organic phase was separated from the aqueous phase, and washed with 600 milliliters of saturated aqueous sodium bicarbonate solution, and then subjected to vacuum distillation. A forerun (65°-79° C., 1.3-1 mm. Hg.) was taken in the amount of 14.0 grams, and discarded. A final product amounting to 103.0 L grams (63% yield) having a boiling point of 80° to 95° C. at 1.0 to 0.8 mm mercury was recovered. The infrared spectrum of this product was identical to that of an authentic sample of methyl phenylglyoxylate.

It will thus be seen that the present invention provides a method for preparing glyoxylic acids and their derivatives which is fast, efficient and does not require the use of starting materials which are difficult to obtain.

The objects set forth above, among those made apparent from the preceding description are, therefore, effectively attained and, since certain changes may be made in the above method without departure from the scope of the invention, it is intended that all matter contained in the above description shall be interpreted as illustrative and not in a limiting sense.

What is claimed is:

1. An improved method for preparing glyoxylic acids and their derivatives which comprises:
   (a) reacting an acyl nitrile compound with concentrated sulfuric acid in the presence of halogen anion to form a first reaction product; and
   (b) reacting said first reaction product with a compound of the general formula

R OH wherein R is hydrogen, a straight or branched-chain hydrocarbon or aralalkyl, provided, however, that ROH is not a tertiary alcohol, to form the acid, amide or ester.

2. The method of claim 1 wherein said compound of the general formula ROH is an alcohol.

3. The method of claim, 2 wherein said alcohol is selected from the group consisting of methanol and ethanol.

4. The method of claim 2 wherein said acyl nitrile compound is a benzoyl cyanide.

5. The method of claim 4 wherein the halogen anion is bromide, and the acylating agent is acetic anhydride.

6. The method of claim 1 wherein said further treatment comprises diluting said first reaction product with water and precipitating therefrom the glyoxamide of said acyl nitrile compound.

7. A method for preparing an arylglyoxylate from an aroyl nitrile compound which comprises the steps of:
   (a) reacting said aroyl nitrile compound with concentrated sulfuric acid in the presence of halogen anion to form a first reaction product; and
   (b) reacting said first reaction product with an alcohol to form said arylglyoxylate; provided, however, that said alcohol is not a tertiary alcohol.

8. The method of claim 7 wherein said halogen anion is selected from the group consisting of fluoride, chloride, bromide and iodide.

9. The method of claim 8 wherein said halogen anion is selected from the group consisting of chloride and bromide.

10. The method of claim 7 wherein the reaction between said aroyl nitrile compound and said concentrated sulfuric acid is conducted in the presence of a hydrocarbon solvent.

11. The method of claim 10 wherein said hydrocarbon solvent is hexane.

12. The method of claim 7 wherein step (a) is conducted in the presence of an acylating agent.

13. The method of claim 12 wherein said acylating agent is present in an amount ranging from about 0.5 to about 1.5 molar equivalents based on the amount of nitrile compound.

14. The method of claim 13 wherein said acylating agent is a compound selected from the group consisting of acetic anhydride, benzoyl chloride, benzoic anhydride and propionic anhydride.

15. The method of claim 14 wherein said aroyl nitrile compound is a benzoyl cyanide and said alcohol is selected from the group consisting of methanol and ethanol.

16. The method of claim 15 wherein said acylating agent is acetic anhydride.

* * * * *

UNITED STATES PATENT AND TRADEMARK OFFICE
CERTIFICATE OF CORRECTION

PATENT NO. : 4,234,739
DATED : November 18, 1980
INVENTOR(S) : James M. Photis, Fred S. Eiseman, Sidney M. Gister It is certified that error appears in the above-identified patent and that said Letters Patent are hereby corrected as shown below:

Col. 1, line 20, "3,5312,737" should be -- 3,532,737 --.

Col. 8, line 29, "1.0 grams" should be -- 1.0 mole --.

Col. 8, line 56, delete "L" at end of line.

Signed and Sealed this

Seventh Day of April 1981

[SEAL]

*Attest:*

RENE D. TEGTMEYER

*Attesting Officer*   *Acting Commissioner of Patents and Trademarks*

Notice of Adverse Decision in Interference

In Interference No. 100,858, involving Patent No. 4,234,739, J. M. Photis, F. S. Eiseman and S. M. Gister, METHOD FOR PREPARING GLYOXYLIC ACIDS AND DERIVATIVES THEREOF, final judgement adverse to the patentees was rendered Dec. 17, 1984, as to claims 6 and 13–16.

[*Official Gazette September 17, 1985.*]